United States Patent [19]

Torra et al.

[11] Patent Number: 5,433,121
[45] Date of Patent: Jul. 18, 1995

[54] CENTER CORE EXTRACTING DRILL BIT

[76] Inventors: Alessandro Torra, 26 Bixby St., Revere, Mass. 02151; Gerardo DeRosa, 33 Cedrus Ave., Roslindale, Mass. 02131

[21] Appl. No.: 158,437

[22] Filed: Nov. 29, 1993

[51] Int. Cl.6 .............................................. G01N 1/04
[52] U.S. Cl. .................................... 73/864.43; 408/205; 408/208
[58] Field of Search ........... 73/864.43, 864.44, 864.45; 175/20, 58; 408/204, 205, 207, 208, 703; 172/22

[56] References Cited

U.S. PATENT DOCUMENTS

| | | | |
|---|---|---|---|
| 1,139,198 | 5/1915 | Lund | 408/208 |
| 1,926,038 | 9/1933 | Culshaw | 255/67 |
| 4,071,099 | 1/1978 | Hensel, Jr. | 175/59 |
| 4,345,484 | 8/1982 | Gould et al. | 73/864.43 |
| 4,534,231 | 8/1985 | Jonsson et al. | 73/864.43 |
| 4,848,484 | 7/1989 | Clements | 175/20 |

FOREIGN PATENT DOCUMENTS

| | | | |
|---|---|---|---|
| 59759 | 1/1968 | Germany | 73/863.43 |
| 684372 | 9/1979 | U.S.S.R. | 175/20 |
| 1157390 | 5/1985 | U.S.S.R. | 73/864.44 |

*Primary Examiner*—Hezron E. Williams
*Assistant Examiner*—Nashmiya Ashraf
*Attorney, Agent, or Firm*—Jacobson, Price, Holman & Stern

[57] ABSTRACT

A core extracting drill bit is provided including an elongated hollow body including a forward cutting end and a second rearward rotary torque input end. The body defines a central chamber therein opening forwardly outwardly through the forward cutting end thereof and one side of the body includes an opening formed therein opening laterally into the central chamber. An elongated closure is provided for the opening with coacting portions of one end of the closure and the body releasably locking the one closure end to the body against radial outward displacement relative thereto and the other of the body and adjacent body portions include structure for keying the other closure end to the body for rotation therewith, but allowing radial outward movement of the other closure end relative to the body. A locking sleeve is rotatably mounted on the body and includes portions thereof lapped over the other closure end and adjacent body portions when the sleeve is in the locking position and the sleeve includes a notch formed therein registerable with the other closure end and adjacent opening portions when the sleeve is rotated from the locking position to an open position to thereby enable the second closure end to be displaced laterally outwardly of the corresponding opening portion through the sleeve notch.

6 Claims, 1 Drawing Sheet

CENTER CORE EXTRACTING DRILL BIT

BACKGROUND OF THE INVENTION

Field of the Invention

This invention relates to a core extracting drill bit for use in sampling meats and other food products and includes a forward cutting tip opening rearwardly into a generally cylindrical chamber, the drill bit having a lateral opening formed in one side thereof opening into the chamber and a removable closure for the opening. The closure for the opening and the opposite ends of the opening include coacting key structure whereby the front of the closure is keyed within the forward portion of the opening for rotation with the drill bit and against lateral outward movement of the front end of the closure relative to the front end of the opening. Further, the rear end of the closure and the rear end of the opening include further coacting key structure whereby the rear end of the closure is keyed within the rear end of the opening for rotation with the drill bit, but in a manner such that lateral outward movement of the rear end of the closure is permitted relative to the rear end of the opening. A sleeve is mounted on the drill bit for rotation relative thereto with the front end of the sleeve lapped over the rear ends of the closure and the opening and one peripheral portion of the sleeve includes a notch registerable with the rear end of the closure and the rear portion of the opening when the sleeve is in a predetermined release position of rotation relative to the bit and the sleeve and bit include coacting structure fictionally retaining the sleeve in adjusted rotated position on the bit.

Description of Related Art

Various different forms of sampling bits and other structures including some of the general structural and operational features of the instant invention heretofore have been known. Examples of these previously known structures are disclosed in U.S. Pat. Nos. 1,926,038, 4,071,099, 4,345,484, 4,534,231 and 4,848,484.

The basic structure of U.S. Pat. No. 4,848,484 is similar to the structure of the instant invention, but the closure member for the access opening thereof requires somewhat more complex structure for releasably locking the cover in a closed position and such locking structure is subject to malfunction if rotated at high speed by a power motor.

SUMMARY OF THE INVENTION

A generally cylindrical bit is provided including at least one peripheral cutting edge on its forward end and defining a core cavity therein opening through the forward end of the bit. In addition, the bit includes a lateral opening formed therein opening into the sample cavity and a closure member is provided for the lateral opening. The closure member and lateral opening are elongated and the front end of the closure member locks into the front end of the lateral opening by lengthwise engagement of the front end of the closure member into the front end of the lateral opening while the rear end of the closure member locks into the rear end of the lateral opening upon lateral displacement of the rear end of the closure into the rear end of the lateral opening. A sleeve is rotatably mounted on the bit and includes a front end which laps over the rear end of the closure and the rear end of the lateral opening and the sleeve includes a notch in one peripheral portion thereof registerable with the rear end of the closure and the rear end of the lateral opening and through which the rear end of the closure is laterally displaceable, the sleeve and bit including coacting structure at least frictionally resisting angular displacement of the sleeve on the bit.

The main object of this invention is to provide a sampling bit capable of removing a core of material into which the bit is advanced and with the bit including means for quickly opening and quickly closing the sample cavity of the bit whenever desired.

Another object of this invention is to provide a sampling bit in accordance with the preceding object and wherein locking structure for retaining the closure for the sample cavity or chamber in the closed position thereof comprises only a single element shiftably supported from the bit.

Yet another object of this invention is to provide a bit in accordance with the preceding objects and wherein the single moveable element for locking the closure in a closed position comprises a sleeve mounted on the bit for angular displacement relative thereto.

A final object of this invention to be specifically enumerated herein is to provide a core sampling bit in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
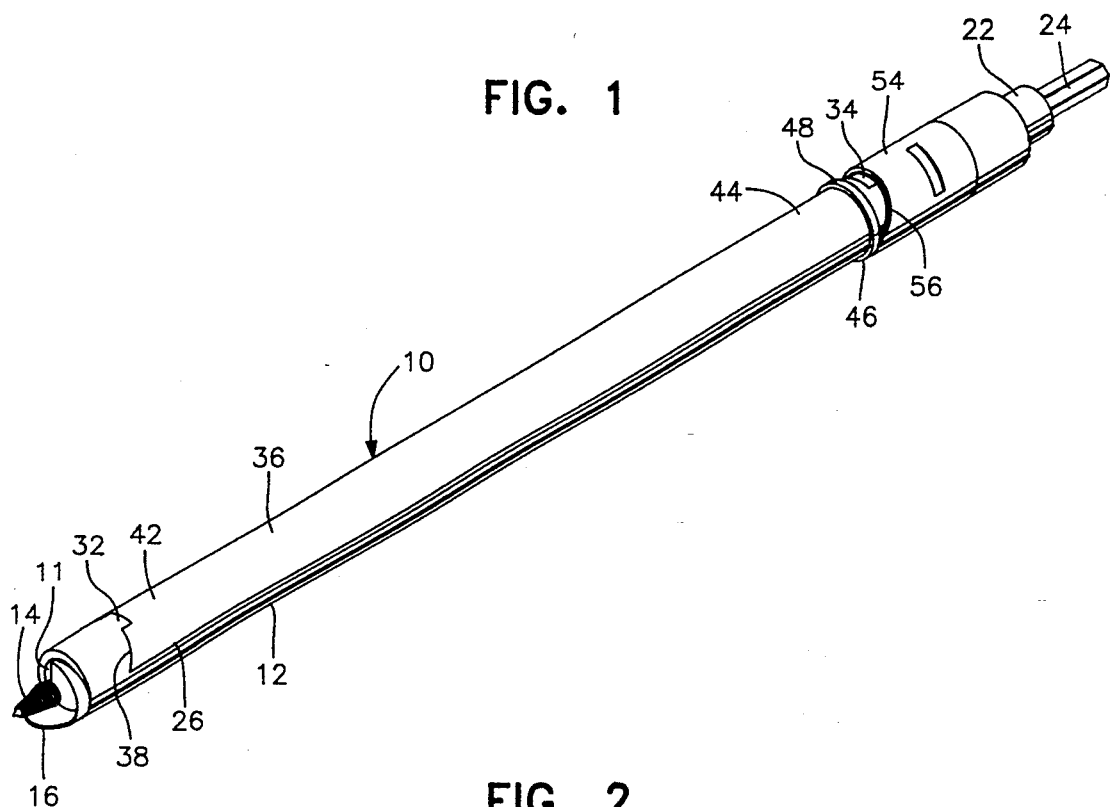
FIG. 1 is a perspective view of the core sampling or extracting drill bit of the instant invention.

Referring now more specifically to the drawings the numeral 10 generally designates the center core extracting drill bit of the instant invention.

The drill bit 10 incorporates an elongated generally cylindrical body 12 which is open at its forward end as at 11 and provided with a center auger screw member 14 supported from a diametric web 15 and at least one outer peripheral cutting edge 16. The rear end of the cylindrical body is externally threaded as at 18 and is removably threadedly seated within a threaded blind bore formed in the forward end of a support body 22 including a rearwardly projecting noncircular drive input shank 24 removably engageable with a drill chuck or the like.

The body 12 includes a lateral opening 26 formed therein including front and rear ends 28 and 30 with a center lug 32 carried by the body 12 projecting into the forward end 28 of the opening 26 and a similar lug 34 projecting into the rear end 30 of the opening 26.

A semicylindrical Closure member 36 is provided for removably closing the opening 26 and the front end of the closure member 36 is inclined as at 38 to match the bevel of the opening front end 28 and includes a central notch 40 formed therein whereby the elongated closure member 36 may be keyed into position relative to the front end 28 of the opening 26 by longitudinal advancement of the front end 42 of the closure member 36 into the forward extremity of the opening 26. In addition, the rear end 44 of the closure member 36 is bevelled to match the bevel of the opening rear end 30 and includes a notch 50 for receiving the lug 34, the rear end 44 being laterally displaceable into the rear end of the opening 26 for keyed engagement of the rear end 44 with the body 12 for rotation therewith.

Figure 2:
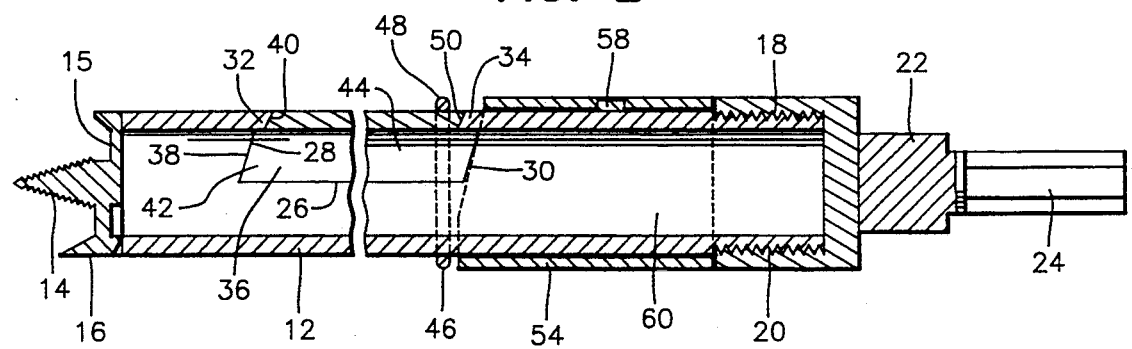
FIG. 2 is an enlarged fragmentary longitudinal vertical sectional view of the drill bit.
Figure 3:
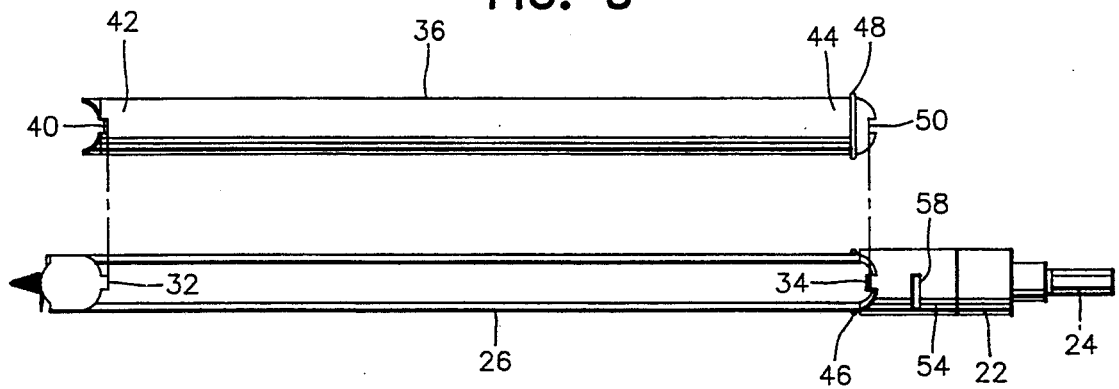
FIG. 3 is a reduced scale plan view of the drill bit oriented as illustrated in FIG. 1 and with the removable closure for the core sample receiving cavity in exploded position.

The body 12 includes a semicircular half ring 46 secured thereto and the closure member 36 includes a semicircular half ring 48 secured thereto with the half rings 46 and 48 being coextensive when the closure member 36 is in the closed position illustrated in FIGS. 1 and 2.

A locking sleeve 54 is rotatably mounted on the body 12 between the half rings 46 and 48 and the forward end of the support body 22. One peripheral portion of the locking sleeve 54 includes a notch 56 registerable with the rear end 30 of the opening 26 and through which the rear end of the closure member 36 may be displaced laterally outwardly of the position thereof illustrated in FIG. 2, the locking sleeve 54 including an inwardly biased portion 58 there of frictionally engaged with the body 12 in order to frictionally resist angular displacement of the locking sleeve 54 about the body 12. However, when the locking sleeve 54 is rotated 180° relative to the body 12 from the position thereof illustrated in FIG. 2, the front end of the locking sleeve 54 laps over the rear end 44 of the closure member 36 and prevents lateral disengagement of the rear end 44 outwardly of the rear end 30 of the opening 26. In this manner, the closure member 36 is locked in the closed position thereof and for rotation with the body 12.

In operation, a motor or manually driven chuck may be engaged with the shank 24 and the drill bit 10 may be forwardly advanced into the material from which a core sample is to be taken.

After the forward end of the drill bit 10 has been advanced the desired amount into the material from which a sample is to be taken and the core sample has moved axially rearwardly past the cutting edge 16 and diametric web 15 into the chamber 60 within the body 12, the bit 10 may be backed out of the material. Thereafter, the locking sleeve 54 may be rotated 180° to the position thereof illustrated in FIG. 2 and the rear end 44 of the closure member 36 may be slightly laterally displaced outwardly of the opening 26. Then, the closure member 36 may be rearwardly displaced relative to the body 12 in order to disengage the front end 42 of the closure member 36 from the front end 28 of the opening 26 and the core sample within the chamber 60 may then be manually removed therefrom laterally through the opening 26. If desired, the bit 10 may be thoroughly cleaned after removing a core sample therefrom and the closure member 36 may then be repositioned to close the opening 26 and the locking sleeve 54 may be rotated 180° from the position thereof illustrated in FIG. 2 in order to lock the rear end of the closure member 36 against lateral displacement out of the rear end 30 of the opening 26.

The foregoing is considered as illustrative only of the principles of the invention. Further, since numerous modifications and changes readily will occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A center core extracting drill bit including an elongated body defining a longitudinal center axis and having a first forward cutting end and a second rearward rotary torque input end, said first forward cutting end including at least one cutting edge for cutting a core while being rotated about said center axis, said body defining a central chamber therein opening forwardly through said first forward cutting end of said body past said cutting edge for receiving a core cut by said cutting edge, said body defining an elongated, longitudinally extending lateral opening formed therein on one side of said body spaced rearward of said forward cutting end and forward of said rotary torque input end, opening laterally into said central chamber and including front and rear ends, an elongated closure for said lateral opening including front and rear ends, said front ends of said opening and closure including first coacting rearwardly and forwardly facing, respectively, key means engageable with each other, upon forward shifting of said closure front end towards said opening front end, to key said closure front end to said body for rotation therewith and against lateral outward movement of said closure front end from said front end of said opening, said rear ends of said opening and closure including second coacting key means engageable with each other, upon lateral inward movement of said closure rear end into said opening rear end, to key said closure rear end to said body for rotation therewith while allowing ready lateral outward movement of said closure rear end from said opening rear end, a locking sleeve including forward and rearward ends rotatably mounted on said body with said forward end of said locking sleeve lapped over said closure and opening rear ends preventing lateral outward movement of said closure rear end from said opening rear end, one side of said forward end of said sleeve including a notch formed therein selectively moveable into and out of registry with said opening rear end upon rotary adjustment of said sleeve about said body, said sleeve and body including coacting means operative to releasably retain said sleeve in predetermined rotated position on said body with said notch out of registry with said rear ends of said closure and opening.

2. The drill bit of claim 1 including means on said body operative to maintain axial positioning of said sleeve on said body.

3. The drill bit of claim 1 wherein said elongated body and second rearward rotary torque input end are separately formed and include coacting means removably supporting said second rearward rotary torque input end from said body.

4. The drill bit of claim 1 wherein said first and second means include endwise outwardly opening notches formed in said closure and axially projecting lugs carried on said body removably received in said notches.

5. The drill bit of claim 4 including means on said body operative to maintain axial positioning of said sleeve on said body.

6. The drill bit of claim 5 wherein said elongated body and second rearward rotary torque input end are separately formed and include coacting means removably supporting said second rearward rotary torque input end from said body.

* * * * *